United States Patent
Den Boef et al.

(10) Patent No.: US 8,868,387 B2
(45) Date of Patent: Oct. 21, 2014

(54) METHOD OF OPTIMIZING A MODEL, A METHOD OF MEASURING A PROPERTY, A DEVICE MANUFACTURING METHOD, A SPECTROMETER AND A LITHOGRAPHIC APPARATUS

(75) Inventors: Arie Jeffrey Den Boef, Waalre (NL); Hugo Augustinus Joseph Cramer, Eindhoven (NL); Jouke Krist, Eindhoven (NL); Willem Jan Grootjans, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 1589 days.

(21) Appl. No.: 12/247,371

(22) Filed: Oct. 8, 2008

(65) Prior Publication Data
US 2009/0094005 A1    Apr. 9, 2009

Related U.S. Application Data

(60) Provisional application No. 60/960,645, filed on Oct. 9, 2007.

(51) Int. Cl.
| | | |
|---|---|---|
| *G06F 7/50* | (2006.01) | |
| *G06F 17/10* | (2006.01) | |
| *G06G 7/48* | (2006.01) | |
| *G01J 3/00* | (2006.01) | |
| *G06F 17/50* | (2006.01) | |
| *G01B 11/24* | (2006.01) | |
| *G03F 7/20* | (2006.01) | |
| *G01N 21/47* | (2006.01) | |
| *G01N 21/956* | (2006.01) | |
| *G01N 21/25* | (2006.01) | |

(52) U.S. Cl.
CPC ........ *G03F 7/70625* (2013.01); *G06F 17/5009* (2013.01); *G01B 11/24* (2013.01); *G06F 17/10* (2013.01); *G01N 21/47* (2013.01); *G01N 21/95607* (2013.01); *G01N 21/255* (2013.01)
USPC ..................... 703/6; 703/2; 356/51

(58) Field of Classification Search
CPC .... G06F 17/5009; G06F 17/10; G01N 21/255
USPC ........................................ 703/2, 6
See application file for complete search history.

(56) References Cited

U.S. PATENT DOCUMENTS

| | | | | |
|---|---|---|---|---|
| 5,459,677 | A  * | 10/1995 | Kowalski et al. ................ | 703/2 |
| 2005/0118735 | A1 * | 6/2005 | Mantz et al. ..................... | 438/5 |

(Continued)

FOREIGN PATENT DOCUMENTS

EP       1 628 164 A2     2/2006

OTHER PUBLICATIONS

Wolfgang Theiss, "Analysis of optical spectra by computer simulation—from basics to batch mode", Nov. 25, 2002.*

(Continued)

*Primary Examiner* — Omar Fernandez Rivas
*Assistant Examiner* — Angel Calle
(74) *Attorney, Agent, or Firm* — Sterne, Kessler, Goldstein & Fox P.L.L.C.

(57) ABSTRACT

A set of parameters used in a model of a spectrometer includes free parameters and fixed parameters. A first set of values for the parameters is set and the model is used to generate a first spectrum. A value of one of the fixed parameters is changed and a second spectrum is generated. An inverse of the model of the spectrometer is then applied to the second spectrum to generate a set of values for the parameters, the values being the same as the first set of values except for one or more of the free parameters. If the free parameter has significantly changed the fixed parameter is designated a free parameter.

40 Claims, 3 Drawing Sheets

(56) References Cited

U.S. PATENT DOCUMENTS

| | | | |
|---|---|---|---|
| 2006/0192936 A1* | 8/2006 | Schenau et al. | 355/69 |
| 2007/0201788 A1* | 8/2007 | Liu et al. | 385/12 |
| 2008/0049214 A1* | 2/2008 | Maznev et al. | 356/51 |
| 2008/0270091 A1* | 10/2008 | Ramanujam et al. | 703/6 |
| 2009/0157360 A1* | 6/2009 | Ye et al. | 703/2 |

OTHER PUBLICATIONS

Nasa, "Spectral Fitting and XSPEC", Oct. 6, 2006.*

K. Kearns, F. Primini, and D. Alexander, "Bias-Free Parameter estimation with few counts, by iterative chi-squared minimization", 1995.*

* cited by examiner

Prior Art

Prior Art

METHOD OF OPTIMIZING A MODEL, A METHOD OF MEASURING A PROPERTY, A DEVICE MANUFACTURING METHOD, A SPECTROMETER AND A LITHOGRAPHIC APPARATUS

CROSS REFERENCE TO RELATED APPLICATIONS

This application claims the benefit under 35 U.S.C. §119 (e) to U.S. Provisional Patent Application No. 60/960,645, filed Oct. 9, 2007, which is incorporated by reference herein in its entirety.

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example, the overlay error between successive layers formed in or on the patterned substrate. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate may be determined. This may be done, for example, by comparing the reflected beam with data stored in a library of known measurements associated with known substrate properties. Two main types of scatterometer are known. Spectroscopic scatterometers direct a broadband radiation beam onto the substrate and measure the spectrum (e.g., intensity as a function of wavelength) of the radiation scattered into a particular narrow angular range. Angularly resolved scatterometers use a monochromatic radiation beam and measure the intensity of the scattered radiation as a function of angle.

Models are often used to simulate results from scatterometers or spectrometers. To determine a critical dimension, a modeled signal may be matched to a measured signal. Within the model there are many parameters (e.g., the thickness or reflectivity of layers of the substrate) which may be varied to generate a modeled spectrum which matches the measured signal. With many different parameters varying freely the matching process is extremely time consuming to run. Too many free parameters may result in an unstable matching process or erroneous set of parameters due to the fact that there may exist more than one combination of these parameters that have virtually equal modeled spectra. Consequently, many of the parameters are often fixed while just a few are varied. However, it may be difficult to determine which parameters may be left free while the others are fixed.

There may be some correlation between the impact of different parameters on the modeled spectrum and present methods of determining which parameters to leave free involve the use of a cross-correlation matrix. A value for each of the parameters is selected and a base spectrum generated. A parameter is varied by a small amount, another spectrum is generated and the change of the spectrum is determined. This is repeated for each of the parameters and the resulting spectra changes between the different parameters are compared to generate the cross-correlation matrix. If a high correlation between two parameters is found at most one of them should be left free. However, while this correlation matrix supports the selection of free and fixed parameters, the use is limited since it may not show the impact of correlation between the spectral change for more than two parameters, it does not give any indication of the impact of the noise in the measured signal on the model with a specific free parameter selection nor does it show the impact of errors in the value of the fixed parameters on the free parameters during the matching process or on the quality of the match.

Furthermore the cross-correlation matrix provides no information about the effect of converting a free parameter to a fixed parameter. Changing a free parameter to a fixed parameter or vice versa could have an unexpected effect on other parameters.

SUMMARY

Therefore, what is needed is an effective system and method of modeling a spectra with an improved methodology of free parameter selection.

In an embodiment of the present invention, there is provided a method of optimizing a model of a spectrometer, the spectrometer being configured to measure a property of a substrate, the model having at least two parameters, the parameters including a first free parameter of which the method includes setting a first set of values for the parameters, generating a first simulated spectrum of the spectrometer from the first set of values using the model, changing the value of a second parameter by a first predetermined amount to form a second set of values for the parameters, the second parameter not being the free parameter, and generating a second simulated spectrum of the spectrometer from the second set of values using the model. The method continues by using a second model to find a third set of values for the parameters from the second simulated spectrum, the second model being arranged such that the third set of values generates substantially the second simulated spectrum using the first model and such that the third set of parameters are the same as the first set of parameters except for the first free parameter, determining the difference between the first free parameter in the third set of values for the parameters and the free parameter in the first set of values, and using the difference as a figure of merit for the choice of free and fixed parameters in the model.

Further embodiments, features and advantages of the present invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example only, with reference to the accompanying drawings in which corresponding reference symbols indicate corresponding parts. Further, the accompanying drawings, which are incorporated herein and form part of the specification, illustrate the present invention and, together with the description, further serve to explain the principles of the invention and to enable a person skilled in the relevant art(s) to make and use the invention.

Figure 1A:
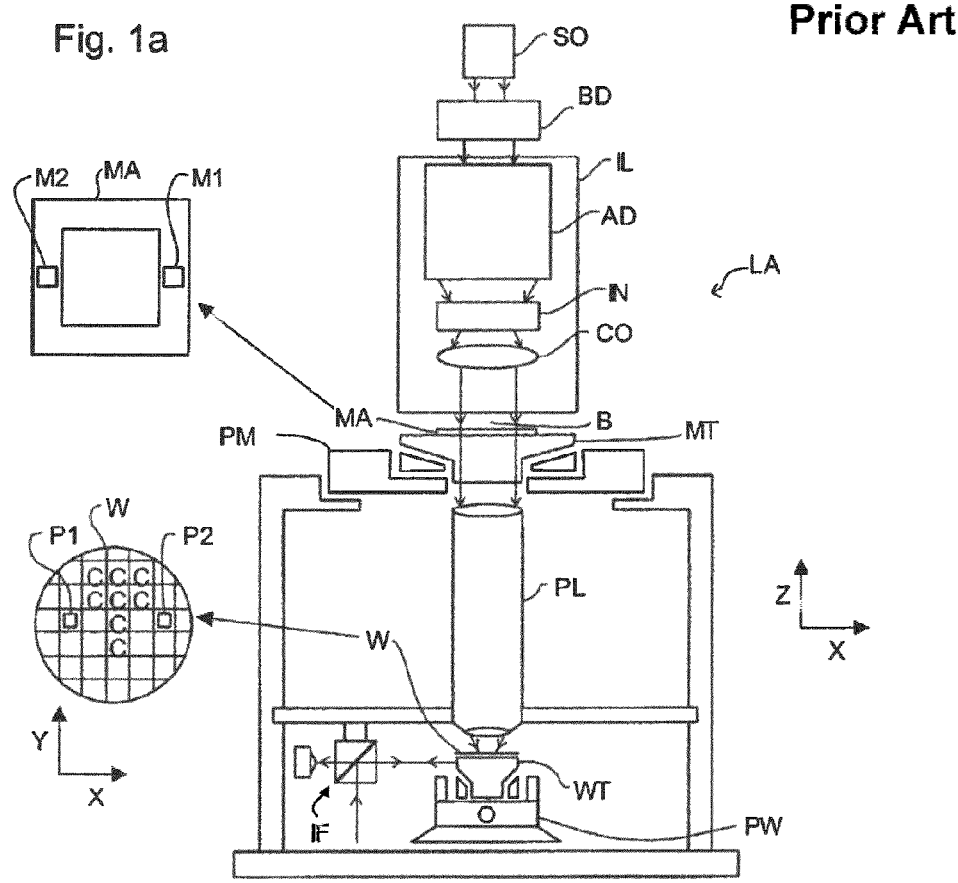
FIG. 1a depicts a lithographic apparatus in accordance with an embodiment of the present invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

Overview

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to affect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1a schematically depicts a lithographic apparatus. The apparatus includes an illumination system (illuminator) IL configured to condition a radiation beam B (e.g., UV radiation or DUV radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist-coated wafer) W and connected to a second positioner PW configured to accurately position the substrate in accordance with certain parameters; and a projection system (e.g., a refractive projection lens system) PL configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device (e.g., mask) MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the support structure (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure (e.g., mask table) MT may be connected to a short-stroke actuator only, or may be fixed. Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies.

The depicted apparatus could be used in at least one of the following modes:

1. In step mode, the support structure (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure (e.g., mask table) MT and the substrate table WT are scanned synchronously while a pattern imparted to the radiation beam is projected onto a target portion C (i.e., a single dynamic exposure). The velocity and direction of the substrate table WT relative to the support structure (e.g., mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
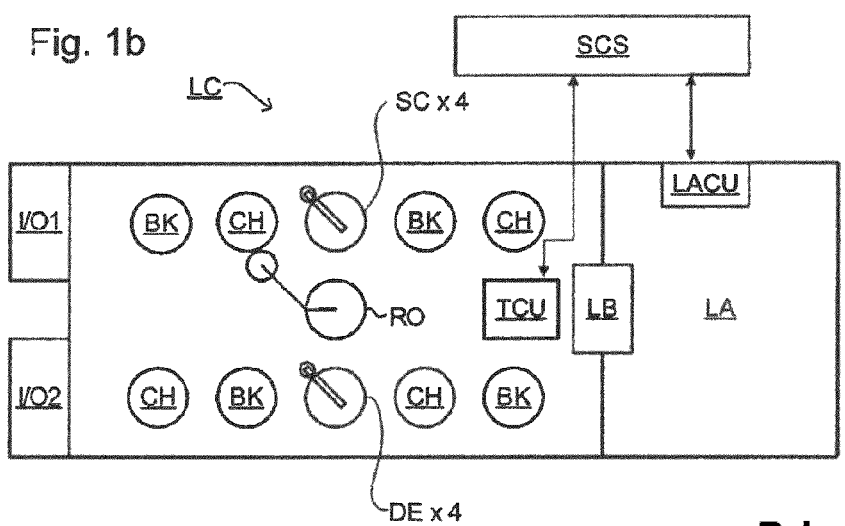
FIG. 1b depicts a lithographic cell or cluster in accordance with an embodiment of the present invention.

As shown in FIG. 1b, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked, e.g., to improve yield, or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast, such that there is only a very small difference in refractive index between the parts of the resist which have been exposed to radiation and those which have not, and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

Figure 2:
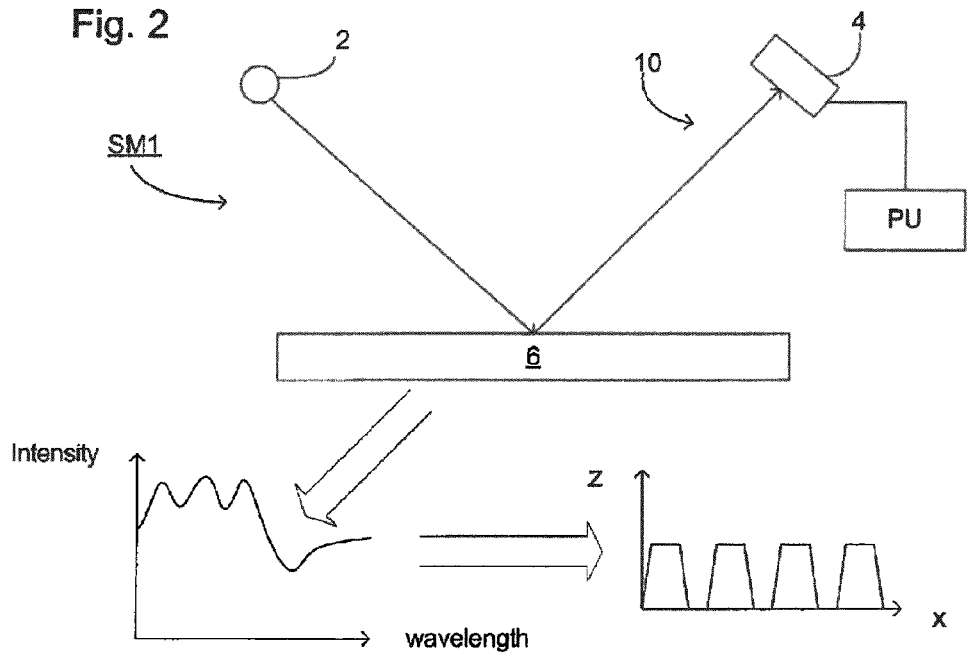
FIG. 2 depicts a first scatterometer in accordance with an embodiment of the present invention.

FIG. 2 depicts a scatterometer SM1 which may be used in an embodiment of the present invention. It includes a broadband (white light) radiation projector 2 which projects radiation onto a substrate 6. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 2. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 3:
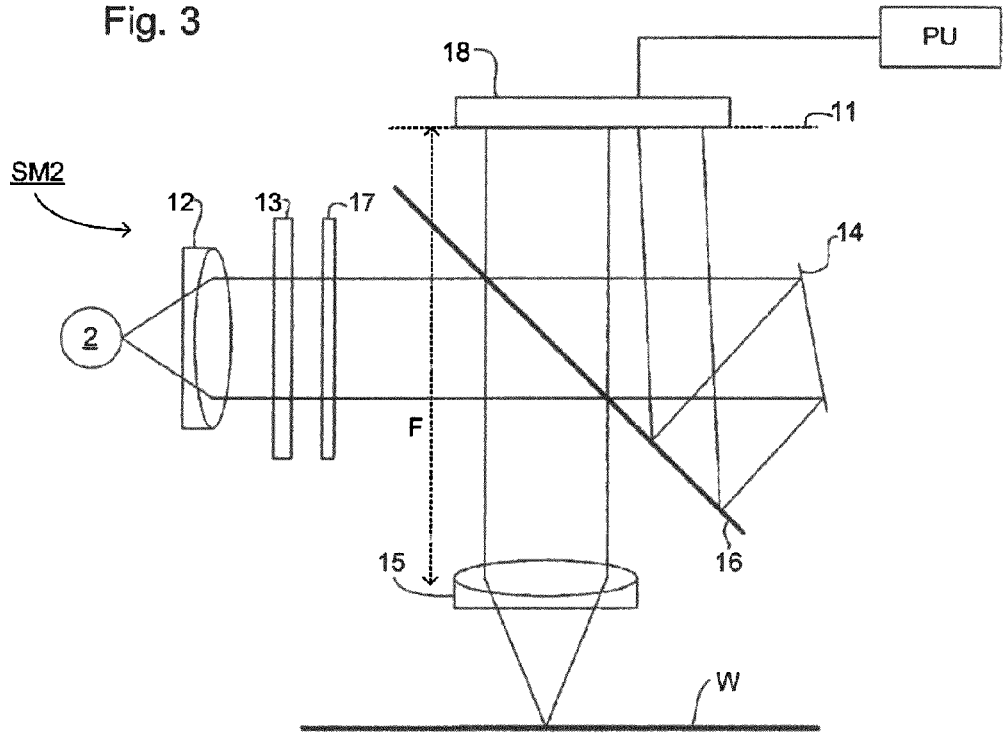
FIG. 3 depicts a second scatterometer in accordance with an embodiment of the present invention.

Another scatterometer that may be used with an embodiment of the present invention is shown in FIG. 3. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), for example, preferably at least about 0.9, and more preferably at least about 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. In one example, the detector is a two-dimensional detector so that a two-dimensional angular scatter spectrum of the substrate target can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, for example, about 405-790 nm or even lower, for example, such as about 200-300 nm. The interference filter may be tunable rather than including a set of different filters. A grating could be used instead of interference filters.

The detector 18 may measure the intensity of scattered light at a single wavelength, or narrow wavelength range, the intensity separately at multiple wavelengths or integrated over a wavelength range. Furthermore, the detector may separately measure the intensity of transverse magnetic and transverse electric polarized light and/or the phase difference between the transverse magnetic- and transverse electric-polarized light.

Using a broadband light source (i.e., one with a wide range of light frequencies or wavelengths, and therefore of colors) is possible, which gives a large etendue, allowing the mixing of multiple wavelengths. The plurality of wavelengths in the broadband each has a bandwidth of 8% and a spacing of at least $2\delta\lambda$ (i.e., twice the bandwidth). A plurality of "sources" of radiation may be different portions of an extended radiation source which have been split using fiber bundles. In this way, angle resolved scatter spectra can be measured at multiple wavelengths in parallel. A 3-D spectrum, for example, such as wavelength and two different angles, can be measured, which contains more information than a 2-D spectrum. This allows more information to be measured which increases metrology process robustness. This is described in more detail in European Patent No. 1,628,164A, which is incorporated by reference herein in its entirety.

The target on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 4:
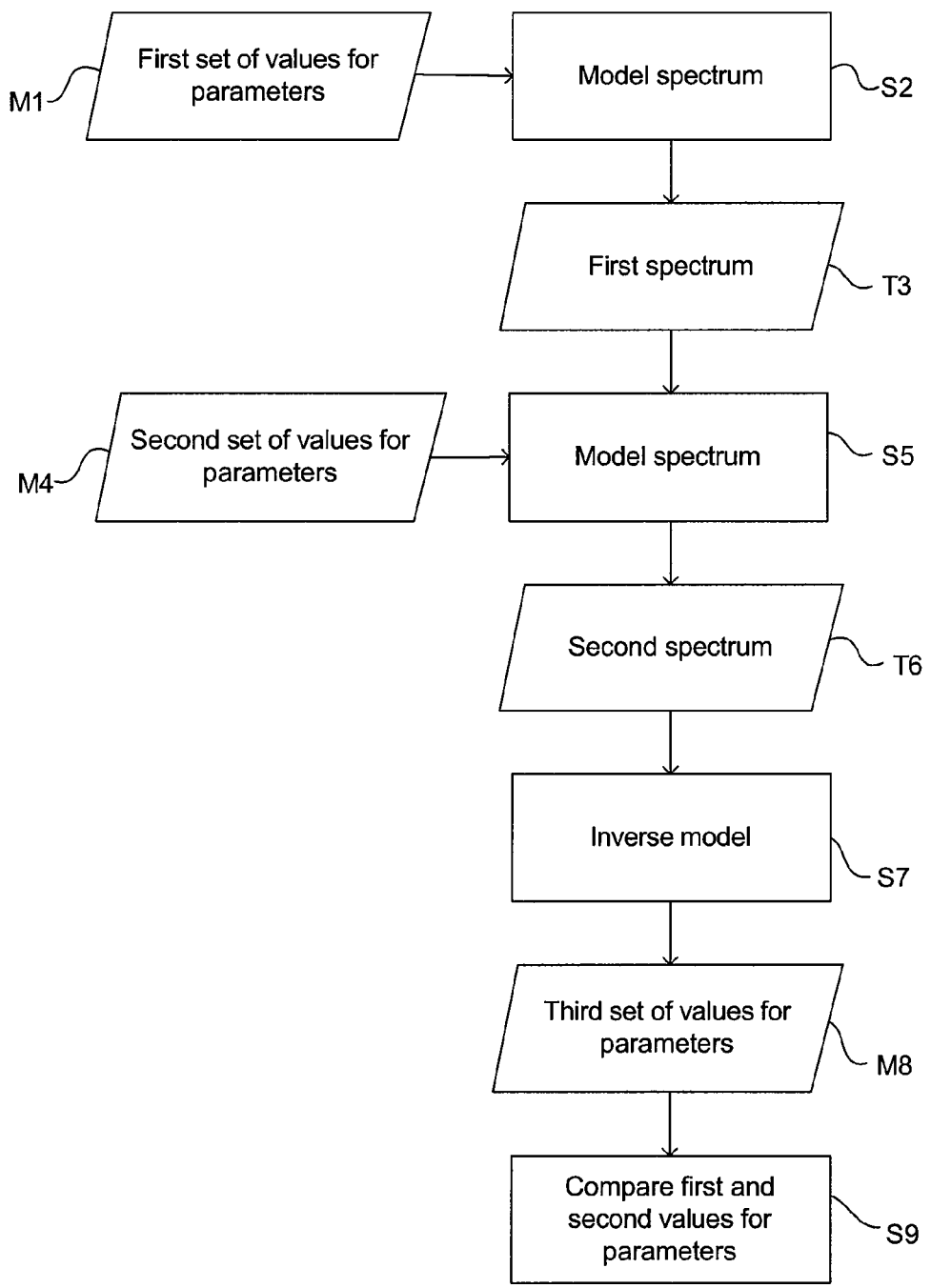
FIG. 4 depicts a process according to an embodiment of the present invention.

Referring to FIG. 4, the parameters used in a spectrometer such as the thickness of layers of the substrate are measured or estimated by the user. These values are input into a model, S2 of the spectrometer as a first set of values, M1 for the parameters to generate a modeled spectrum, T3.

One or more of the parameters is designated a free parameter and the remaining parameters are designated as fixed parameters. One of the fixed parameters is changed by a small amount, for example, by an amount representative of the variation or error in the determination of the fixed parameter, to form a second set of values, M4 and the model of the spectrometer run again, S5. This generates a second spectrum, T6 which will differ from the first spectrum.

An inverse of the model of the spectrometer is then applied, S7 to the second spectrum, with the fixed parameters being the same values as the values from the first set of values, M1. However, as the spectrum differs from the first spectrum the free parameter will differ and thus a third set of values, M8 for the parameters will be generated. The first and third set of values are then compared, S9. If the value for any of the free parameters differs significantly between the first and third set of data, it indicates that the measured values for the free parameters are highly sensitive to errors in the fixed parameters. Thus, even a small error in the estimated or measured value for this fixed parameter would lead to a significant error in the resulting measurement of the free parameters. If the difference between one or more of the free parameters in the first and third set of data exceeds a predetermined level, then the chosen designation of free and fixed parameters is rejected. The same second spectrum can be used to generate further sets of values, each set of values being the same as the first set of values except for the designated free parameters, the set of free parameters which differs being a different set for each set of values.

Using the model the third set of values may be used to generate a spectrum. This may be compared to the spectrum generated using the first set of values to give a further indication of the merit of selection of free parameters.

This process is repeated for each of the fixed parameters in relation to all chosen sets of free parameters.

In another embodiment, the model of the spectrometer and a given profile may be linearized for small changes in the model parameters. Linearization may drastically increase the speed of generating new spectra and doing the inverse modeling.

Two predictions may be made from the model regarding error contributions in the free parameters. The first concerns in what magnitude errors in the fixed parameters are transferred into errors in the free parameters (and hence in the measurements). The error in the fixed parameter may be estimated if its source is known, it may be metrology noise, or process variations. With the proposed method we know the impact on the free parameters. The second concerns variations in the intensity as seen by detector 4. The source of these variations may be, for example, photon noise or vibrations in the metrology tool and the magnitude of the variations may be determined from repeatability measurements. Using the present invention, noise on the intensity can be translated into noise on the free parameters. How the intensity noise is translated into noise on the free parameters is dependent on the choice of free parameters. The choice of the fixed and free parameters in the model may be based upon an optimal balance between the two error contributions.

In addition to the fixed parameters and free parameters, there may also be dependent parameters which are coupled to the free parameters, for example, being a fixed proportion of the free parameters. The same method may be applied to determine the impact of the coupling between the dependent parameters and the free parameters on the sensitivity of the free parameters and the dependent parameters to variations on the fixed parameters.

This method may be applied to many different types of parameters such as the thickness of layers of the substrate, reflectivity of layers of the substrate, the refractive index and absorption coefficient of materials used and parameters indicating the shape of the measured structure, as well as parameters in the spectrometry model such as the gain of the photon detector.

In another embodiment, an approximation to an inverse of a model of the spectrometer may be often used, for example, especially an inverse of a linearized version of the model.

The spectrometer may include a data handling unit configured to optimize a model of the spectrometer. The data handling unit may include a readable medium encoded with machine executable instructions configured to optimize the model of the spectrometer.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional storing building blocks illustrating the implementation of specified functions and relationships thereof. The boundaries of these functional storing building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of optimizing a model of a spectrometer, the spectrometer being configured to measure a property of a substrate, the model having at least two input parameters, the input parameters comprising a first free input parameter and a fixed input parameter, the method comprising:
    setting, using a processing device, a first set of values for the input parameters;
    generating, using a processing device, a first simulated spectrum of the spectrometer from the first set of values using the model;
    changing, using a processing device, the value of a second input parameter by a first predetermined amount to form a second set of values for the input parameters, the second input parameter being different from the free input parameter;
    generating, using a processing device, a second simulated spectrum of the spectrometer from the second set of values using the model;
    using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;
    determining, using the processing device, a difference between the first free input parameter in the third set of values for the input parameters and the free input parameter in the first set of values; and
    selecting, using a processing device, the free and fixed input parameters in the model based on the difference.

2. The method according to claim 1, wherein the selecting includes using the magnitude of the difference as a determining factor for the choice of the free and fixed input parameters in the model.

3. The method according to claim 1, wherein the selecting comprises determining whether the difference between the first free input parameter in the third set of values for the input parameters and the free input parameter in the first set of values differ by more than a second predetermined amount and if the difference is greater than the second predetermined amount, the second input parameter is designated a free input parameter in the model.

4. The method according to claim 1, further comprising:
    generating a third simulated spectrum of the spectrometer from the third set of values; and
    comparing the first simulated spectrum and the third simulated spectrum and selecting the free and fixed input parameters based on the difference.

5. The method according to claim 4, wherein the selecting includes using the difference as a second figure of merit for the choice of the free and fixed input parameters.

6. The method according to claim 1, wherein the model includes a plurality of input parameters, the method further comprising repeating the changing, the generating, the using and the determining for each input parameter which has not previously been designated a free input parameter in the model, wherein during each repetition the value of a different second input parameter which has not previously been designated a free input parameter is changed in the changing.

7. The method according to claim 4, wherein the model includes a plurality of input parameters, the method further comprising repeating the changing, the generating, the using and the determining for each free input parameter, wherein during each repetition in the changing the set of third values is the same as the first set of values except for a first free input parameter, the first free input parameter changing for each repetition.

8. The method according to claim 1, wherein the second model is the inverse of the model.

9. The method according to claim 1, wherein the second model is the inverse of a linear version of the model.

10. The method according to claim 1, wherein the first predetermined amount is a percentage of the second input parameter.

11. The method according to claim 3, wherein the second predetermined amount is a percentage of the first free input parameter.

12. The method according to claim 1, wherein one of the input parameters is the thickness of a layer forming part of the substrate.

13. The method according to claim 1, wherein the model comprises dependent input parameters, the dependent input parameters being related to at least one free input parameter by a predetermined relationship.

14. A method of configuring a spectrometer, comprising a method of optimizing a model of a spectrometer, the spectrometer being configured to measure a property of a substrate, the model having at least two input parameters, the input parameters comprising a first free input parameter and a fixed input parameter, the method comprising:
    setting, using a processing device, a first set of values for the input parameters;
    generating, using a processing device, a first simulated spectrum of the spectrometer from the first set of values using the model;
    changing, using a processing device, the value of a second input parameter by a first predetermined amount to form a second set of values for the input parameters, the second input parameter being different from the free input parameter;
    generating, using a processing device, a second simulated spectrum of the spectrometer from the second set of values using the model;
    using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;
    determining, using the processing device, a difference between the first free input parameter in the third set of values for the input parameters and the free input parameter in the first set of values; and
    selecting, using a processing device, the free and fixed input parameters in the model based on the difference.

15. A method of measuring a property of a substrate comprising configuring a spectrometer according to claim 14 and measuring a reflected spectrum.

16. A device manufacturing method comprising:
    using a lithographic apparatus to form a pattern on a substrate; and
    determining a property of the pattern printed by a method including:
    optimizing a model of a spectrometer, the spectrometer being configured to measure a property of a substrate, the model having at least two input parameters, the input parameters comprising a first free input parameter and a fixed input parameter, the method comprising:
    setting, using a processing device, a first set of values for the input parameters;
    generating, using a processing device, a first simulated spectrum of the spectrometer from the first set of values using the model;
    changing, using a processing device, the value of a second input parameter by a first predetermined amount to form a second set of values for the input parameters, the second input parameter being different from the free input parameter;
    generating, using a processing device, a second simulated spectrum of the spectrometer from the second set of values using the model;
    using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;
    determining, using the processing device, a difference between the first free input parameter in the third set of values for the input parameters and the free input parameter in the first set of values;
    selecting, using a processing device, the free and fixed input parameters in the model based on the difference; and
    measuring, using the processing device, a spectrum reflected by the pattern on the substrate.

17. A spectrometer configured to measure a property of a substrate, the apparatus comprising:
    a radiation projector configured to project a radiation onto a substrate;
    a detector configured to detect the radiation reflected from the substrate; and
    a data handling unit configured to optimize a model of the spectrometer, the model having at least two input parameters, the input parameters comprising a first free input parameter and a fixed input parameter, the method comprising:
    setting a first set of values for the input parameters;
    generating a first simulated spectrum of the spectrometer from the first set of values using the model;
    changing the value of a second input parameter by a first predetermined amount to form a second set of values for the input parameters, the second input parameter being different from the free input parameter;
    generating a second simulated spectrum of the spectrometer from the second set of values using the model;
    using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;
    determining a difference between the first free input parameter in the third set of values for the input parameters and the free input parameter in the first set of values; and
    selecting the free and fixed input parameters in the model based on the difference.

18. The spectrometer according to claim 17, wherein the selecting includes using the magnitude of the difference as a determining factor for the choice of free and fixed input parameters.

19. The spectrometer according to claim 17, wherein the data handling unit includes a readable medium encoded with machine executable instructions configured to optimize the model of the spectrometer.

20. A lithographic apparatus comprising:
    an illumination system arranged to illuminate a pattern;
    a projection system arranged to project an image of the pattern onto a substrate; and an angularly resolved spectrometer configured to measure a property of a substrate, the spectrometer comprising:
a radiation projector configured to project a radiation onto a substrate;
a detector configured to detect the radiation reflected from the substrate; and
a data handling unit configured to optimize a model of the spectrometer, the model having at least two input parameters, the input parameters comprising a first free input parameter and a fixed input parameter, the method comprising:
setting a first set of values for the input parameters;
generating a first simulated spectrum of the spectrometer from the first set of values using the model;
changing the value of a second input parameter by a first predetermined amount to form a second set of values for the input parameters, the second input parameter being different from the free input parameter;
generating a second simulated spectrum of the spectrometer from the second set of values using the model;
using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;
determining a difference between the first free input parameter in the third set of values for the input parameters and the free input parameter in the first set of values; and
selecting the free and fixed input parameters in the model based on the difference.

21. A method of optimizing a model of a spectrometer, the spectrometer being configured to measure a property of a substrate, the model having at least two input parameters, the input parameters comprising a first free input parameter and a fixed input parameter, the method comprising:
setting a first set of values for the input parameters;
automatedly generating a first simulated spectrum of the spectrometer from the first set of values using the model;
changing the value of a second input parameter by a first predetermined amount to form a second set of values for the input parameters, the second input parameter being different from the free input parameter;
automatedly generating a second simulated spectrum of the spectrometer from the second set of values using the model;
using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;
determining a difference between the first free input parameter in the third set of values for the input parameters and the free input parameter in the first set of values; and
selecting the free and fixed input parameters in the model based on the difference.

22. The method of claim 21, wherein the selecting includes using the magnitude of the difference as a determining factor in the choice of the free and fixed input parameters in the model.

23. The method of claim 21, wherein the selecting comprises determining whether the difference between the first free input parameter in the third set of values for the input parameters and the free input parameter in the first set of values differ by more than a second predetermined amount and if the difference is greater than the second predetermined amount, the second input parameter is designated a free input parameter in the model.

24. The method of claim 21, further comprising:
generating a third simulated spectrum of the spectrometer from the third set of values; and
comparing the first simulated spectrum and the third simulated spectrum and selecting the free and fixed input parameters based on the difference.

25. The method of claim 24, wherein the selecting includes using the difference as a second figure of merit for the choice of the free and fixed input parameters.

26. The method of claim 21, wherein the model includes a plurality of input parameters, the method further comprising repeating the changing, the generating, the using and the determining for each input parameter which has not previously been designated a free input parameter in the model, wherein during each repetition the value of a different second input parameter which has not previously been designated a free input parameter is changed in the changing.

27. The method of claim 24, wherein the model includes a plurality of input parameters, the method further comprising repeating the changing, the generating, the using and the determining for each free input parameter, wherein during each repetition in the changing the set of third values is the same as the first set of values except for a first free input parameter, the first free input parameter changing for each repetition.

28. The method of claim 21, wherein the second model is an inverse of the model.

29. The method of claim 21, wherein the second model is an inverse of a linear version of the model.

30. The method of claim 21, wherein the first predetermined amount is a percentage of the second input parameter.

31. The method of claim 23, wherein the second predetermined amount is a percentage of the first free input parameter.

32. The method of claim 21, wherein one of the input parameters is a thickness of a layer forming part of the substrate.

33. The method of claim 21, wherein the model comprises dependent input parameters, the dependent input parameters being related to at least one free input parameter by a predetermined relationship.

34. A method of configuring a spectrometer comprising a method of optimizing a model of a spectrometer, the spectrometer being configured to measure a property of a substrate, the model having at least two input parameters, the input parameters comprising a first free input parameter and a fixed input parameter, the method comprising:
setting a first set of values for the input parameters;
automatedly generating a first simulated spectrum of the spectrometer from the first set of values using the model;
changing the value of a second input parameter by a first predetermined amount to form a second set of values for the input parameters, the second input parameter being different from the free input parameter;
automatedly generating a second simulated spectrum of the spectrometer from the second set of values using the model;
using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;

determining a difference between the first free input parameter in the third set of values for the input parameters and the free input parameter in the first set of values; and selecting the free and fixed input parameters in the model based on the difference.

35. A method of optimizing a model of a spectrometer, the spectrometer being configured to measure a property of a substrate, the model having at least two input parameters, the input parameters comprising a first free input parameter and a fixed input parameter, the method comprising:

setting a first set of values for the input parameters;

automatedly generating a first simulated spectrum of the spectrometer from the first set of values using the model;

changing the value of a second input parameter by a first predetermined amount to form a second set of values for the input parameters, the second input parameter being different from the free input parameter;

automatedly generating a second simulated spectrum of the spectrometer from the second set of values using the model;

using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;

determining a difference between the first free input parameter in the third set of values for the input parameters and the free input parameter in the first set of values;

selecting the free and fixed input parameters in the model based on the difference; and measuring a spectrum reflected by the pattern on the substrate, wherein the dependent input parameters are related to at least one free input parameter by a predetermined relationship.

36. A device manufacturing method comprising:

using a lithographic apparatus to form a pattern on a substrate; and determining a property of the pattern printed by a method including optimizing a model of a spectrometer, the spectrometer being configured to measure a property of a substrate, the model having at least two input parameters, the input parameters comprising a first free input parameter and a fixed input parameter, the method comprising:

setting, using a processing device, a first set of values for the input parameters;

generating, using a processing device, a first simulated spectrum of the spectrometer from the first set of values using the model;

changing, using a processing device, the value of a second input parameter by a first predetermined amount to form a second set of values for the input parameters, the second input parameter being different from the free input parameter;

generating, using a processing device, a second simulated spectrum of the spectrometer from the second set of values using the model;

using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;

determining, using the processing device, a difference between the first free input parameter in the third set of values for the input parameters and the free input parameter in the first set of values;

selecting, using a processing device, the free and fixed input parameters in the model based on the difference; and measuring, using the processing device, a spectrum reflected by the pattern on the substrate.

37. A spectrometer configured to measure a property of a substrate, the apparatus comprising:

a radiation projector configured to project a radiation onto a substrate;

a detector configured to detect the radiation reflected from the substrate; and a controller configured to optimize a model of the spectrometer, the model having at least two input parameters, the input parameters comprising a free input parameter, the optimization comprising, setting a first set of values for the input parameters, generating a first simulated spectrum of the spectrometer with the first set of values using the model, changing the value of a second input parameter by a first predetermined amount to form a second set of values for the input parameters, the second input parameter being different from the free input parameter;

generating a second simulated spectrum of the spectrometer with the second set of values using the model, using a second model to calculate a third set of values for the input parameters from the second simulated spectrum, the third set of values generating substantially the second simulated spectrum and such that the third set of input parameters are the same as the first set of input parameters except for the free input parameter, determining a difference between the first free input parameter in the third set of values for the input parameters and the free input parameter in the first set of values, and selecting the free and fixed input parameters in the model based on the difference.

38. The spectrometer of claim 37, wherein the selecting includes using the magnitude of the difference as a determining factor for the choice of free and fixed input parameters.

39. The spectrometer of claim 37, wherein the controller includes a computer readable medium encoded with machine executable instructions configured to optimize the model of the spectrometer.

40. A lithographic apparatus comprising:

an illumination system arranged to illuminate a pattern;

a projection system arranged to project an image of the pattern onto a substrate; and an angularly resolved spectrometer configured to measure a property of a substrate, the spectrometer comprising:

a radiation projector configured to project a radiation onto a substrate;

a detector configured to detect the radiation reflected from the substrate; and a controller configured to optimize a model of the spectrometer, the model having at least two input parameters, the input parameters comprising a first free input parameter and a fixed input parameter, the method comprising:

setting a first set of values for the input parameters;

generating a first simulated spectrum of the spectrometer from the first set of values using the model;
changing the value of a second input parameter by a first predetermined amount to form a second set of values for the input parameters, the second input parameter being different from the free input parameter;
generating a second simulated spectrum of the spectrometer from the second set of values using the model;
using a second model to find a third set of values for the input parameters from the second simulated spectrum, the second model being arranged such that the third set of values generates substantially the second simulated spectrum using the first model and such that the third set of input parameters are the same as the first set of input parameters except for the first free input parameter;
determining a difference between the first free input parameter in the third set of values for the input parameters and the free input parameter in the first set of values; and
selecting the free and fixed input parameters in the model based on the difference.

* * * * *

UNITED STATES PATENT AND TRADEMARK OFFICE
CERTIFICATE OF CORRECTION

PATENT NO. : 8,868,387 B2  
APPLICATION NO. : 12/247371  
DATED : October 21, 2014  
INVENTOR(S) : Den Boef et al.

It is certified that error appears in the above-identified patent and that said Letters Patent is hereby corrected as shown below:

In the Claims

Column 12, line 5, claim 1, please delete "a" (first occurrence) and insert --the--.
Column 12, line 8, claim 1, please delete "a" (first occurrence) and insert --the--.
Column 12, line 13, claim 1, please delete "a" (first occurrence) and insert --the--.
Column 12, line 17, claim 1, after "spectrum," please insert --using the process device,--.
Column 12, line 20, claim 1, after "spectrum" please delete "using the first model".
Column 13, line 16, claim 14, after "spectrometer" please delete ",".
Column 13, line 24, claim 14, after "using" please delete "a" (first occurrence) and insert --the--.
Column 13, line 27, claim 14, after "using" please delete "a" (first occurrence) and insert --the--.
Column 13, line 32, claim 14, after "using" please delete "a" (first occurrence) and insert --the--.
Column 13, line 36, claim 14, after "spectrum," please insert --using the process device,--.
Column 13, line 39, claim 14, after "spectrum" please delete "using the first model".
Column 13, line 46, claim 14, after "using" please delete "a" and insert --the--.
Column 13, line 57, claim 16, after "of" please delete "a" and insert --the--.
Column 13, line 63, claim 16, after "using" please delete "a" (first occurrence) and insert --the--.
Column 13, line 66, claim 16, after "using" please delete "a" (first occurrence) and insert --the--.
Column 14, line 4, claim 16, after "using" please delete "a" (first occurrence) and insert --the--.
Column 14, line 8, claim 16, after "spectrum" please insert --using the process device,--.
Column 14, line 11, claim 16, after "spectrum" please delete "using the first model".
Column 14, line 17, claim 16, after "values;" please insert --and--.
Column 14, line 31, claim 17, after "comprising a" please delete "first".
Column 14, line 32, claim 17, after "the" please delete "method" and insert --optimization--.
Column 14, line 36, claim 17, please delete "from" and insert --with--.
Column 14, line 42, claim 17, please delete "from" and insert --with--.
Column 14, line 43, claim 17, after "model to" please delete "find" and insert --calculate--.
Column 14, line 45, claim 17, after "the" (first occurrence) please delete "second model being arranged such that the".
Column 14, line 46, claim 17, please delete "generates" and insert --generating--.

Signed and Sealed this  
Thirtieth Day of June, 2015

Michelle K. Lee  
*Director of the United States Patent and Trademark Office*

CERTIFICATE OF CORRECTION (continued)
U.S. Pat. No. 8,868,387 B2

Column 14, line 47, claim 17, please delete "using the first model".
Column 14, line 49, claim 17, after "the first" please delete "free".
Column 15, line 9, claim 20, after "comprising a" please delete "first".
Column 15, line 10, claim 20, after "the" delete "method" and insert --optimization--.
Column 15, line 14, claim 20, please delete "from" and insert --with--.
Column 15, line 20, claim 20, please delete "from" and insert --with--.
Column 15, line 21, claim 20, please delete "find" and insert --calculate--.
Column 15, line 23, claim 20, please delete "second model being arranged such that the".
Column 15, line 24, claim 20, please delete "generates" and insert --generating--.
Column 15, line 25, claim 20, please delete "using the first model".
Column 15, line 27, claim 20, after "for the" please delete "first".
Column 15, line 53, claim 21, please delete "using the first model".
Column 16, line 67, claim 34, please delete "using the first model".
Column 17, line 11, claim 35, after "two" please insert --dependent--.
Column 17, line 28, claim 35, please delete "using the first model".
Column 17, line 34, claim 35, after "values;" please insert --and--.
Column 17, line 47, claim 36, please delete "a" and insert --the--.
Column 17, line 49, claim 36, after "the method" please insert --further--.
Column 17, line 49, claim 36, after "comprising" please delete ":" and insert --,--.
Column 17, line 52, claim 36, after "parameters" please delete ";" and insert --,--.
Column 17, line 53, claim 36, please delete "a" (first occurrence) and insert --the--.
Column 17, line 55, claim 36, after "model" please delete ";" and insert --,--.
Column 17, line 60, claim 36, after "parameter" please delete ";" and insert --,--.
Column 17, line 63, claim 36, after "model" please delete ";" and insert --,--.
Column 17, line 65, claim 36, after "spectrum" please insert --using the process device,--.
Column 18, line 1, claim 36, please delete "using the first model".
Column 18, line 3, claim 36, after "parameter" please delete ";" and insert --,--.
Column 18, line 7, claim 36, after "values;" please insert --and--.
Column 18, line 8, claim 36, please delete "a" (first occurrence) and insert --the--.
Column 18, line 9, claim 36, after "difference" please delete ";" and insert --,--.
Column 18, line 58, claim 40, after "comprising" please delete ":" and insert --,--.
Column 18, line 65, claim 40, after "comprising a" please delete "first".
Column 18, line 66, claim 40, after "the" please delete "method" and insert --optimization--.
Column 18, line 66, claim 40, after "comprising" please delete ":" and insert --,--.
Column 19, line 2, claim 40, please delete "from" and insert --with--.
Column 19, line 2, claim 40, after "model" please delete ";" and insert --,--.
Column 19, line 6, claim 40, after "parameter" please delete ";" and insert --,--.
Column 19, line 8, claim 40, after "model" please delete ";" and insert --,--.
Column 19, line 9, claim 40, please delete "find" and insert --calculate--.
Column 19, line 11, claim 40, please delete "second model being arranged such that the".
Column 19, line 19, claim 40, please delete "generates" and insert --generating--.
Column 19, line 13, claim 40, please delete "using the first model".
Column 19, line 15, claim 19, after "for the" please delete "first".
Column 19, line 15, claim 40, after "parameter" please delete ";" and insert --,--.
Column 19, line 19, claim 40, after "values;" please insert --and--.